United States Patent [19]

Wettlaufer et al.

[11] Patent Number: 5,290,765

[45] Date of Patent: *Mar. 1, 1994

[54] METHOD OF PROTECTING BIOLOGICAL MATERIALS FROM DESTRUCTIVE REACTIONS IN THE DRY STATE

[75] Inventors: Scott H. Wettlaufer, Newfield; Aldo C. Leopold, Ithaca, both of N.Y.

[73] Assignee: Boyce Thompson Institute for Plant Research, Inc., Ithaca, N.Y.

[*] Notice: The portion of the term of this patent subsequent to Apr. 1, 2010 has been disclaimed.

[21] Appl. No.: 833,735

[22] Filed: Feb. 11, 1992

Related U.S. Application Data

[63] Continuation-in-part of Ser. No. 678,065, Apr. 1, 1991, Pat. No. 5,200,399, which is a continuation-in-part of Ser. No. 583,858, Sep. 14, 1990, abandoned.

[51] Int. Cl.$^5$ .................. A61K 31/70; A61K 31/715; A61K 35/78
[52] U.S. Cl. ......................... 514/23; 514/53; 514/78; 424/195.1; 427/3; 427/4
[58] Field of Search ............... 514/53, 23, 78; 424/195.1; 427/3, 4

[56] References Cited

U.S. PATENT DOCUMENTS

| | | | |
|---|---|---|---|
| 4,206,200 | 6/1980 | Guthohrlein et al. | 424/9 C |
| 4,559,298 | 12/1985 | Fahy | 435/1 |
| 4,806,343 | 2/1989 | Carpenter et al. | 424/450 |
| 4,824,938 | 4/1989 | Koyama et al. | 530/357 |
| 4,857,319 | 8/1989 | Crowe et al. | 424/94.1 |
| 4,876,241 | 10/1989 | Feldman et al. | 514/2 |
| 4,891,319 | 1/1990 | Roser | 435/188 |
| 4,897,353 | 1/1990 | Carpenter et al. | 424/450 |
| 4,927,763 | 5/1990 | Sudoma | 435/260 |
| 4,931,361 | 6/1990 | Baldeschwieler et al. | 428/482.2 |
| 4,956,295 | 9/1990 | Sudoma | 435/252.1 |
| 5,026,566 | 6/1991 | Roser | 426/443 |
| 5,149,543 | 9/1992 | Cohen et al. | 424/499 |
| 5,149,653 | 9/1992 | Roser | 435/260 |

OTHER PUBLICATIONS

"Stabilization of dry phospholipid bilayers and proteins by sugars", Crowe, et al, Bichem. J. (1987) 242, 1–10.
"Stabilization of phosphofructokinase with sugars drying freeze-drying:" Carpenter, et al, Biochimica et Biophysica Acta 923 (1987) 109–115.
Glass Transistions in Soybean Seed, Bruni, et al, Plant Plant Physiol. (1991) 96, 660–663.
The Glassy State in Corn Embryos, William et al, Plant Physiol. (1989) 89, 977–981.
Lipid–Sugar Interactions, Caffrey, et al, Plant Physiol (1988) 754–758.
Relevance of Amadori and Millard Products to See Deterioration Wettlaufer, et al, Plant Physiol. (1991) 165–169.
Are Freezing and Dehydration Similar Stress Vectors? A Comparison of Modes of Interaction of Stabilizing Solutes with Biomolecules, Crowe, et al, Cryobiology 27, 219,231 (1990).
The Relevance of Cryoprotenctant "Toxicity" to Cryobiology Fahy, Gregory, Cryobiology 23, 1–13 (1986).
Modes of Stabilization of a Protein by Organic Solutions during Desiccation, Carpenter, et al, Cryobiology 25, 459–470 (1988).
Prospects for Vitrification of Whole Organs, Fahy, G., Cryobiology Laboratory), Abstracts, 18th Annual Meeting, p. 167.
Andrews, E., "Geleatin Capsules Revamped For New Generation of Pills", New York Times, Oct. 5, 1992.

Primary Examiner—John W. Rollins
Attorney, Agent, or Firm—Michael F. Brown; Ralph R. Barnard; Christopher A. Michaels

[57] ABSTRACT

A method is provided for protection of biological materials from the stresses of air-drying and also from destructive reactions, such as oxidation and free-radical attack, which degrade the materials during long-term storage. The method involves drying the materials, which may contain potentially destructive agents such as free-radical generators or reducing sugars, in the presence of a vitrifying substance, and under conditions which allow the protective substance to become vitrified.

27 Claims, 8 Drawing Sheets

5,290,765

METHOD OF PROTECTING BIOLOGICAL MATERIALS FROM DESTRUCTIVE REACTIONS IN THE DRY STATE

REFERENCE TO RELATED APPLICATION

This is a continuation-in-part of a co-pending application No. 07/678,065, filed on Apr. 1, 1991, now U.S. Pat. No. 5,200,399, which is a continuation-in-part of co-pending application No. 07/583,858, filed on Sep. 14, 1990, and entitled METHOD OF PROTECTING BIOLOGICAL MATERIALS FROM DESTRUCTIVE REACTIONS IN THE DRY STATE, now abandoned.

BACKGROUND OF THE INVENTION

1. Field of the Invention

This invention relates to the long-term storage of biological materials in a dry state. Particularly, it relates to a method of protecting biological materials from reactions such as oxidation and free-radical attack which can destroy such materials when they are stored for long periods of time, while at the same time protecting them from denaturation and other destruction caused by the drying process itself.

2 Description of the Related Art

Although it is advantageous to be able to store proteins, nucleic acids, cells, and other useful biological products in a dry or frozen state, most such materials lose a significant part of their biochemical activity when subjected to the freezing or drying process. Hence, a body of work has developed in the area of protecting biological materials from the stresses created by the processes of freezing and drying. Most of such work has dealt with freezing and freeze-drying, and only a few studies address the problems involved in air-drying. The patents of Crowe, et al. (U.S. Pat. No. 4,857,316) and Carpenter, et al. (U.S. Pat. Nos. 4,806,343 and 4,897,353) disclose methods of protecting liposomes and proteins, respectively, from the stresses of freezing and freeze-drying. The same group of researchers has also published several papers on the subject, including "Stabilization of Dry Phospholipid Bilayers and Proteins by Sugars" (Biochem. J., vol. 242 (1987), pp. 1-10), "Modes of Stabilization of a Protein by Organic Solutes During Desiccation", Cryobiology, 25:459-470 (1988), and "Cryoprotection of Phosphofructokinase with Sugars During Freeze-Drying . . . ", Biochimica et Biophysica Acta, 923:109-115 (1987). Another group has proposed the use of vitrification as a mechanism to protect blood and whole organs when they are subjected to freezing for long-term storage (Fahy, G. M., "Prospects for Vitrification of Whole Organs", Cryobiology, 18:617-622 (1981); Fahy, G. M., "The Relevance of Cryoprotectant Toxicity to Cryobiology", Cryobiology, 23:1-13 (1986); Fahy, G. M., "Cryopreservation of Biological Materials in a Non-Frozen or Vitreous State," U.S. Pat. No. 4,559,298). (The above publications are hereby incorporated by reference.) However, this proposal has never been extended to other substances, nor to drying, which is not at all feasible for the storage of whole organs.

All of the aforementioned publications focus on the processes of freezing and freeze-drying. The process of drying by exposure to a dessicating material at temperatures above freezing (usually room temperature or above), herein referred to as "air-drying", subjects a biological material to a different set of stresses than those of freezing or freeze-drying. See Crowe, "Are Freezing and Dehydration Similar Stress Vectors? A Comparison of Modes of Interaction of Stabilizing Solutes with Biomolecules", Cryobiology 27:219-231 (1990). This is further demonstrated by the fact that the processes of freeze-drying and air-drying do not have identical effects on biological materials. Whereas sorbitol, a non-vitrifying substance, will protect some biological materials (particularly chloroplast fragments known as thylakoids) from the stresses of freeze-drying, it does not so protect the material during the air-drying process (see experimental results below). Furthermore, whereas the Carpenter patent teaches that transition-metal ions are necessary to protect many proteins when freeze-drying, the work of Roser (U.S. Pat. No. 4,891,319) demonstrates that metal ions are not necessary to protect proteins from the stresses of air-drying.

The aforementioned references, including the Roser patent, address the destructive effects of the preservation process itself, primarily the destruction of the liposome structure and the denaturation of proteins. Prior to the work of the present inventors, little or no work had been done to investigate means for protecting materials from destructive reactions which take place after drying, such as oxidation and free-radical attack. Carpenter discusses the desirability of using a non-reducing sugar as a protectant in his system to avoid the oxidation reaction, but does not propose a method of protecting the proteins from such a reaction when they must be stored in the presence of a reducing sugar.

SUMMARY OF THE INVENTION

This invention sets forth a method of protecting sensitive biological materials during the air-drying process, while simultaneously providing protection for the dried materials from destructive reactions which pose a threat during the storage period. This preserves the utility of such materials over the course of longer storage times than were previously available. The process involves drying the sensitive materials in the presence of a substance which forms a glassy, amorphous solid state, a process known as vitrification, and which in so doing encases the materials and protects them from destructive reactions.

Any compound that achieves a vitrified state, and does not initiate a destructive reaction with the substance to be protected, will serve as a protectant.

It is therefore an objective of this invention to provide a method of protecting biological materials from destruction caused during the process of air-drying.

It is a further objective of this invention to provide a method of protecting biological materials from destructive reactions and forces such as oxidation and free-radical attack.

It is yet a further objective of this invention to provide a method of maintaining biological materials of diverse types in a dry state for long periods of time.

Further objectives may be found in the following drawings, specification and claims.

DETAILED DESCRIPTION OF THE INVENTION

Although the most convenient form of long-term storage for biological materials is in the dry state, at room temperature, many such useful preparations contain compounds or substances that initiate reactions which gradually destroy the utility of the materials over time when stored in this manner. Free-radical generators, such as copper and iron, need be present in only trace amounts to set off chain reactions which destroy materials such as lipids and proteins. Reducing compounds, such as glucose, initiate oxidation reactions in many pharmaceutical preparations and in foods such as dried milk. This is called "browning", for the substances become darker in color as the reaction progresses. Compounds which initiate these reactions are often necessary components of a pharmaceutical preparation or food, or impurities which are very difficult to remove. For this reason, most such products bear an expiration date, which reflects the decreased activity of such compounds due to the progression of destructive reactions.

Exposing a sensitive material which must be dried and stored in the presence of destructive elements or compounds to a vitrifying substance during the drying process protects the material from the stresses of drying, and also from attack by the destructive reactions which would otherwise be initiated and progress during the storage period.

Figure 1:
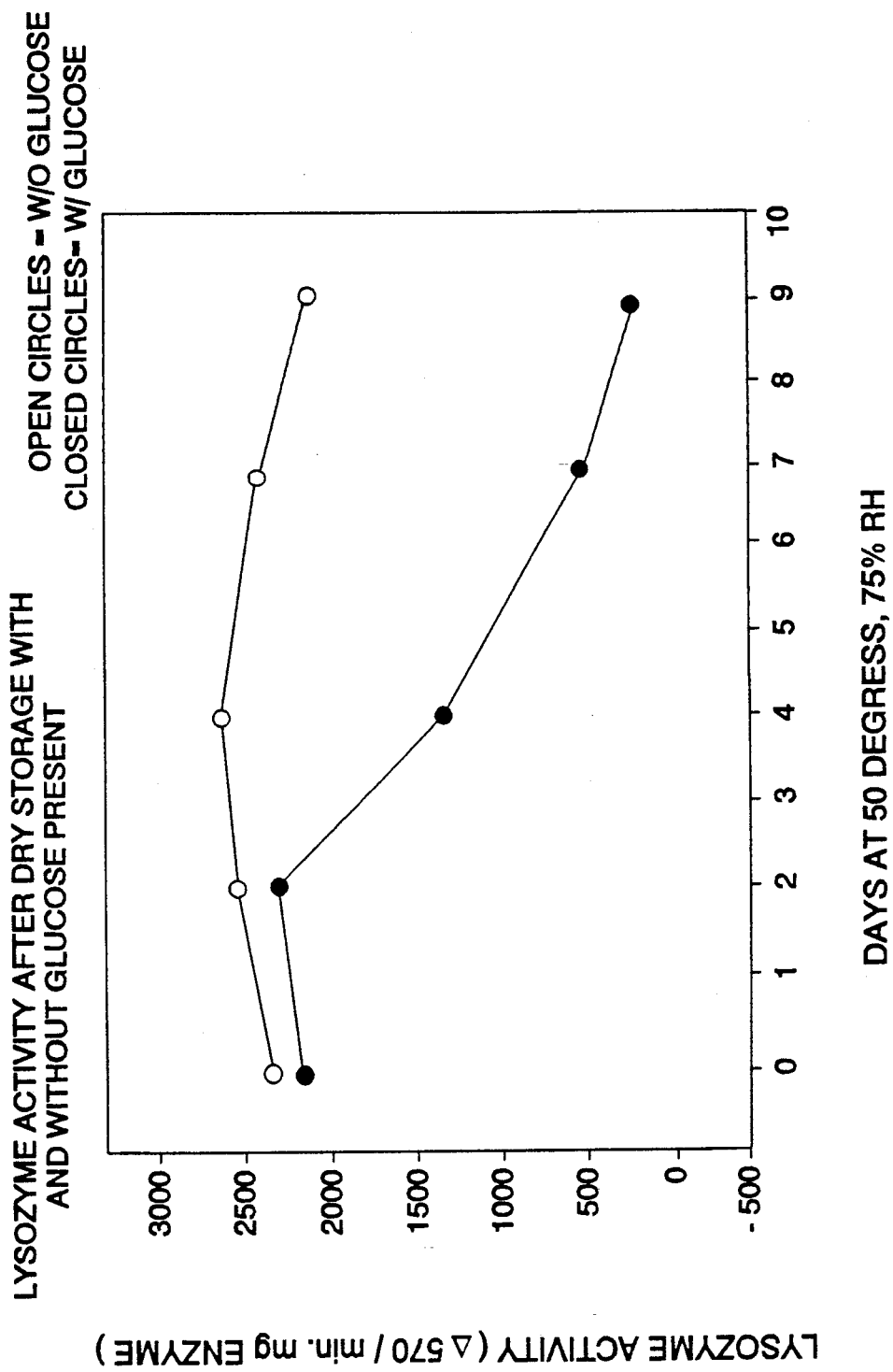
FIG. 1 is a graph depicting the loss of activity of lysozyme when stored in the presence of glucose, a reducing sugar, compared to lysozyme stored without glucose for the same period of time.

For example, lysozyme is an enzyme which is slowly degraded over time when stored in the presence of glucose, a reducing sugar. FIG. 1 depicts the loss of biological activity of the enzyme over time when dried in the presence of glucose, and the corresponding activity when the same enzyme was dried without a reducing sugar present. An oxidation-reduction reaction known as the Amadori reaction, which is initiated by the reducing sugar, causes this loss of activity.

The activity of the enzyme after drying and storage was measured in the following manner. The enzyme was taken up in water and *Micrococcus lysodeikticus* bacteria were added to the solution. This bacterium is destroyed by active lysozyme, and the change in optical density of the solution at 570 $\mu$m over time after the addition of the bacteria was used as a measure of the amount of enzyme activity remaining.

As the graph indicates, with glucose present, very little of the enzyme activity remained after nine days of dry storage at 75% humidity and 50 degrees C. Without any glucose present, almost all of the activity remained.

Figure 2:
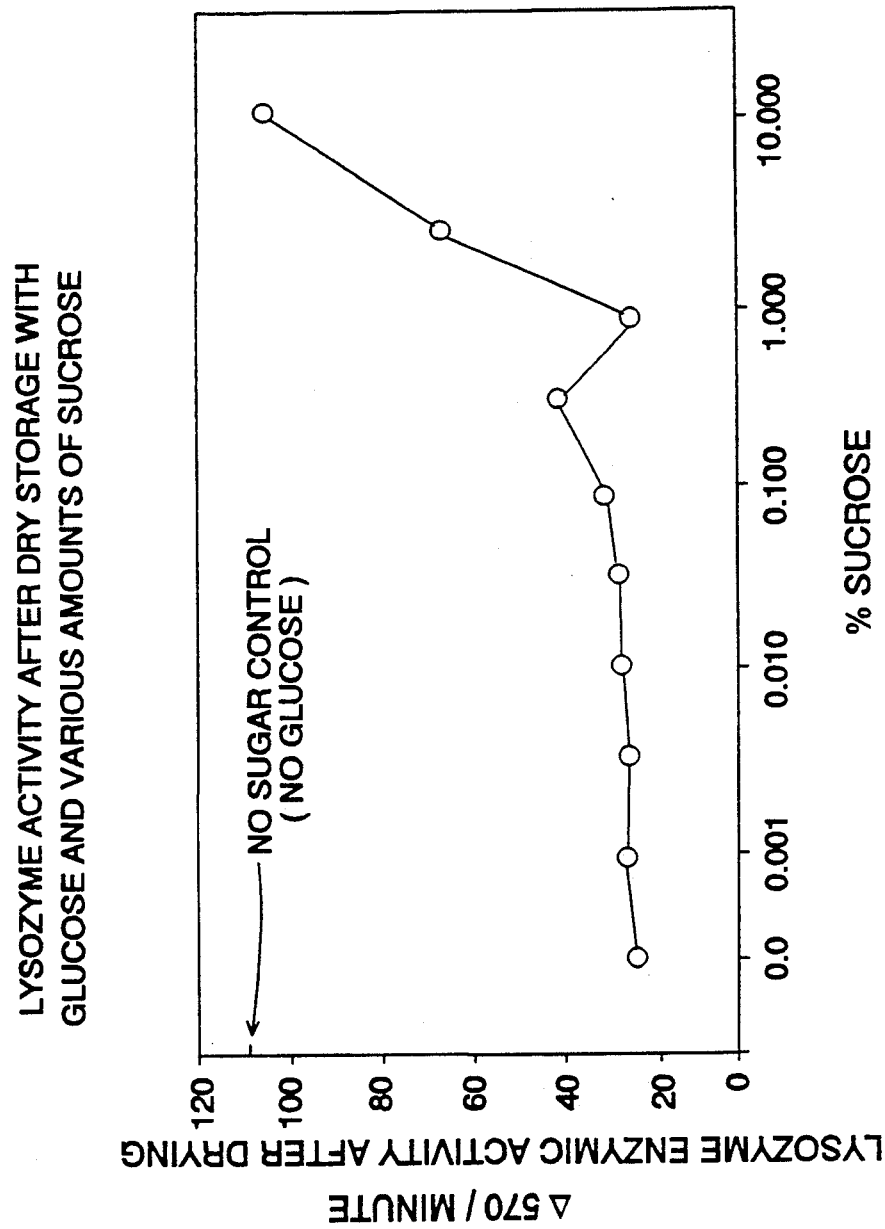
FIG. 2 is a graph depicting the activity of lysozyme when stored for ten days in the presence of glucose (a reducing sugar) along with varying concentrations of sucrose (a vitrifying agent).

FIG. 2 demonstrates the protective activity of sucrose, a vitrifying substance, when added to the mixture outlined above at different concentrations. When dried with glucose but with the vitrifying substance also present, the lysozyme retained 100% of its activity after ten days of storage as above. A concentration somewhere between 1% and 10% by weight of sucrose was required for protective effect, with full protection achieved with a solution of 10% sucrose by weight.

For each experiment, 200 $\mu$g of lysozyme (25 $\mu$l) was combined with 480 $\mu$g of glucose (25 $\mu$l), and one of several concentrations of sucrose. The mix was placed over NaCl (75% Relative Humidity) and incubated at 50 degrees centigrade, and lysozyme activity was then measured by the same assay outlined above.

Vitrifying agents will also protect from the effects of free-radical attack. This is demonstrated by experiments in which lysozyme is dried with the pigment riboflavin and varying concentrations of a sucrose/raffinose combination, and then exposed to light. The light acting on the riboflavin causes the formation of free radicals, which are generally destructive of proteins. However, in the presence of vitrifying agents (sucrose and raffinose), the protein is protected from these free-radical attacks.

For each free-radical experiment, lysozyme (8 mg/ml) was solubilized in a solution of riboflavin (5 mg/ml). 50 mM phosphate, pH 8.5, was added as a buffer. Sucrose and raffinose were mixed together in a 3:1 ratio and solubilized to make a 20% solution. To create varying levels of sugar concentration, the sugar stock was diluted and then mixed with the lysozyme to yield a total of 40 ml of each the following concentrations of sugar after mixing: 0.1%, 0.3%, 1.9%, 3.0%, and 10.0%. In addition, a control solution with no sugar was prepared. The samples were placed in a vacuum desicator over phosphorous pentoxide, under vacuum, for 48 hours at 4 degrees C. to dry. They were then transferred to a desicator containing sodium chloride to equilibrate them to 75% relative humidity for 48 hours at 4 degrees C. After equilibration, half of the samples were assayed for enzymatic activity and the other half were placed under a heliarc lamp (24 inches), on ice, for three hours. They were then assayed for enzymatic activity after warming to room temperature. Note that although sucrose and raffinose are both vitrifiers when used alone, raffinose also inhibits the crystallization of the sucrose, increasing its degree of vitrification.

Figure 3:
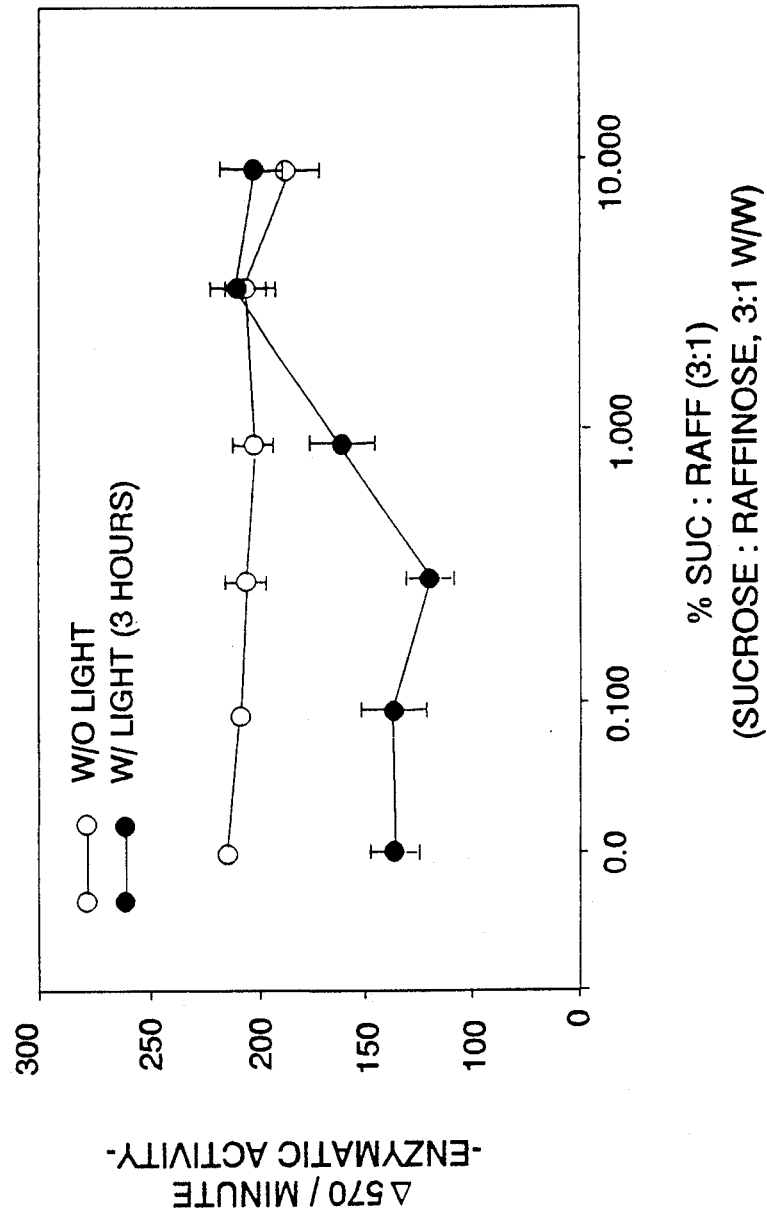
FIG. 3 is a graph depicting the activity of lysozyme when dried in the presence of riboflavin and varying concentrations of a sucrose/raffinose mixture, and then subjected to light.

The results of these experiments are shown in FIG. 3. Each point on the graph represents the average of three experiments, each of which represents the average of three replicates. When the mixtures were not exposed to light (white points), there was very little decrease in enzymatic activity. However, when the mixture was exposed to light, in the absence of a vitrifying agent, enzymatic activity was sharply decreased. This demonstrates the destructive effect of the free-radicals created by the riboflavin when exposed to light. As the concentration of the vitrifying agents was increased, however, this effect was reversed, until at a concentration of 3% sugar, the activity was restored to a level comparable to that existing before illumination (and hence, before free-radical reactions were initiated).

These results demonstrate the use of a vitrifying substance for protection from destructive reactions which degrade sensitive materials during storage. A vitrifying substance also protects enzymes and other materials from losing their activity through the drying process itself. The combination of the two types of protection (from the stresses of drying and from subsequent breakdown reactions) yields a simple system for preservation of biological materials in a dry state.

Figure 4:
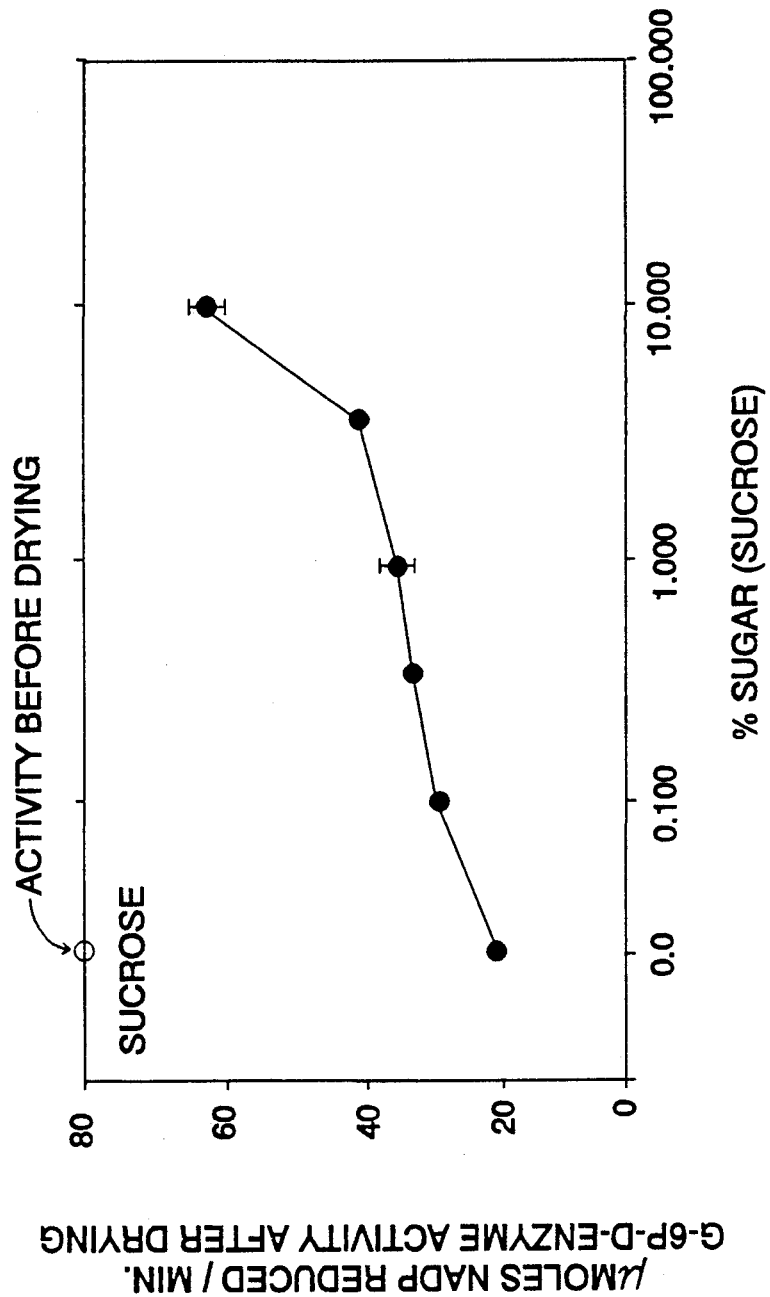
FIG. 4 is a graph depicting the activity of glucose-6-phosphate-dehydrogenase when dried in the presence of various concentrations of sucrose, a vitrifying agent.

To demonstrate the protective effects of vitrifying substances during drying, the enzyme Glucose-6-Phosphate Dehydrogenase (5 µg, 20 µl) was placed in a reaction tube with buffer solution and one of six concentrations of sucrose (0-10% range), and then placed over NaCl and dried as outlined above. Subsequently, the enzyme was taken up in water again and tested for enzymic activity (reduction of NADP). As shown in FIG. 4, in the absence of sucrose, the rehydrated enzyme showed only 25% of its original activity; in the presence of 10% sucrose, the rehydrated enzyme retained 85% of its original activity.

Figure 5:
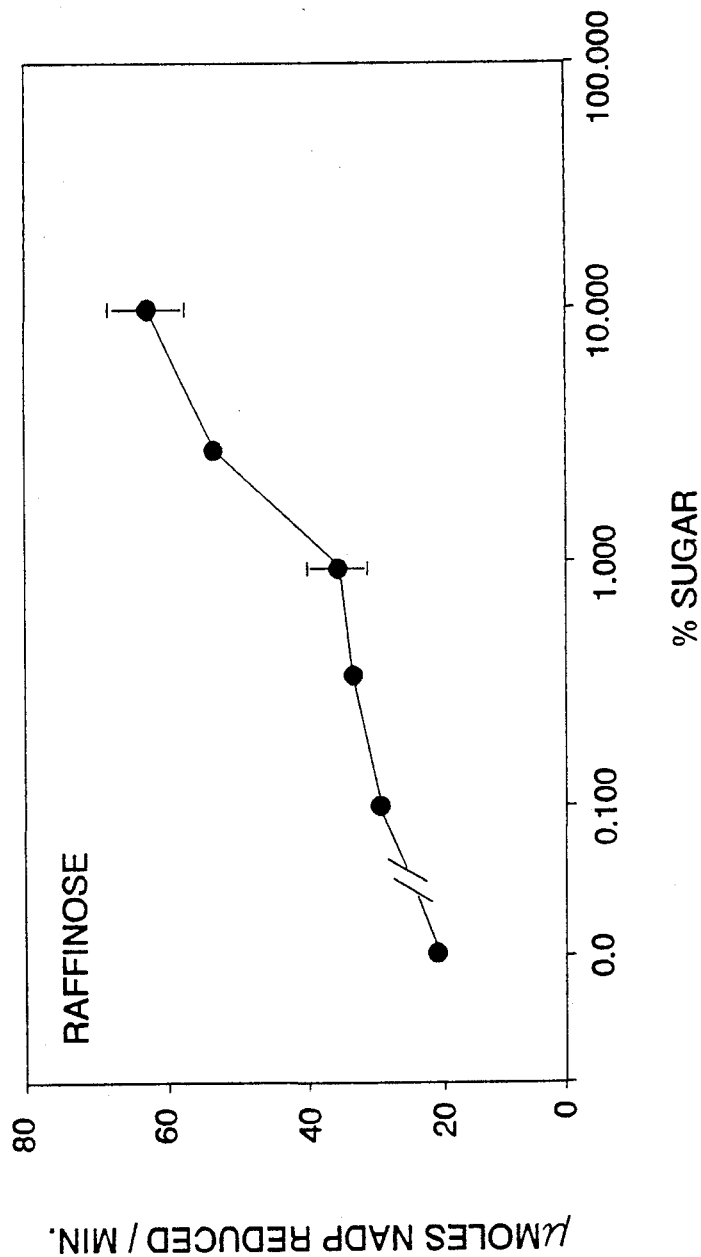
FIG. 5 is a graph depicting the activity of glucose-6-phosphate-dehydrogenase when dried in the presence of various concentrations of raffinose, a vitrifying agent.

This effect may be achieved with any vitrifying substance. FIG. 5 demonstrates the protective effect in the same experimental system when raffinose was used rather than sucrose. The combination of raffinose and sucrose, as noted above, would be particularly effective.

Exposure to a vitrifying substance also serves to protect membranes from the effects of drying. Thylakoid membranes from pea chloroplasts provide a convenient mechanism for assaying the integrity of membranes, because the component reactions of photosynthesis are localized in these membranes and may be easily assayed. Chlorophylls of the photosynthetic apparatus emit small amounts of red light (fluorescence) under all physiological conditions. When dark-adapted thylakoid membranes are exposed to low intensity continuous light, the fluorescence rises from the low initial ($F_O$) level to a maximal ($F_M$) final level (time course about 3-5 seconds). The $F_O$ fluorescence represents the efficiency at which light energy is transferred among antenna protein complexes to the reaction center. A 10% increase in $F_O$ represents about a 2% decrease in the efficiency of transfer and can be attributed to alteration in the interactions between the antenna protein complexes. The change in fluorescence between $F_O$ and $F_M$ is called the variable fluorescence ($F_V$); the amplitude of $F_V$ represents the conversion of light energy into chemical energy in the reaction center complex. A fractional decrease in $F_V$ is indicative of damage to the same fraction of total reaction center.

Figure 6:
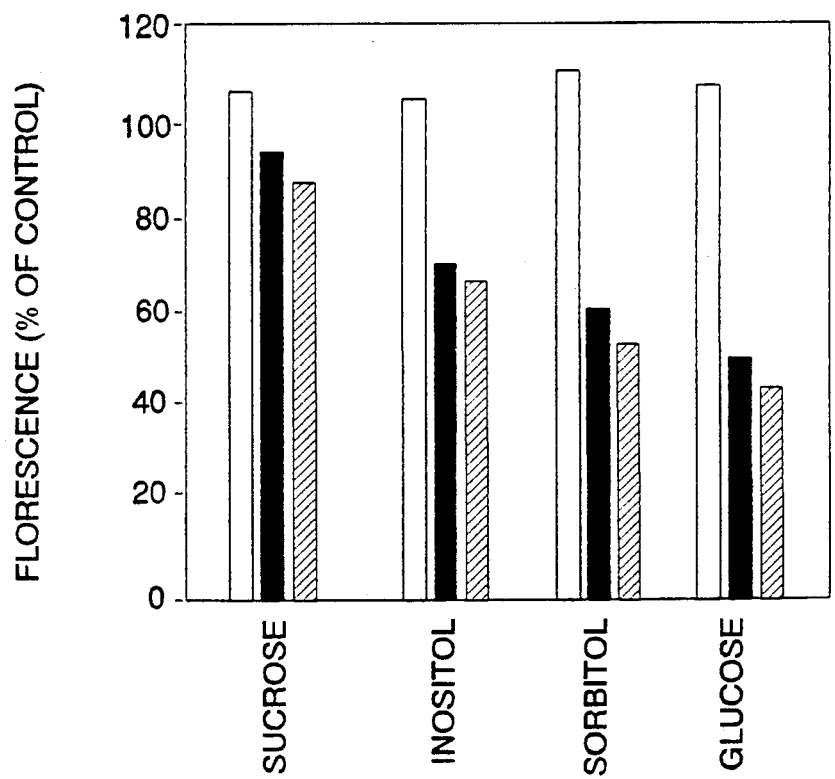
FIG. 6 is a graph depicting the fluorescence of thylakoid membranes when dried in the presence of different substances.

As shown in FIG. 6, when fresh pea thylakoids are dried and stored for 2-6 weeks, then rehydrated, a pronounced decrease is observed in the variable fluorescence. However, when the thylokoids are dried in the presence of a vitrifying substance, such as sucrose, the decrease is markedly reduced. This demonstrates the protection provided by the vitrified substance during drying and storage. The other sugars used, inositol and sorbitol, do not achieve the vitrified state. Although glucose does vitrify, it also acts destructively toward the membranes as noted above.

Figure 7:
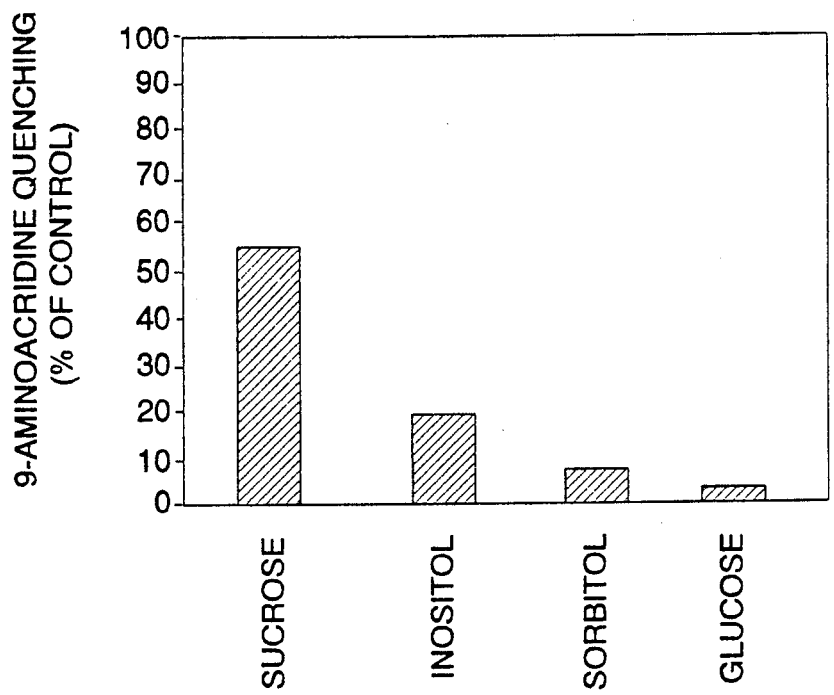
FIG. 7 is a graph depicting the ability of thylakoid membranes to produce a protein gradient in the presence of light, when dried in the presence of various substances.

FIG. 7 depicts another measure of destruction of the thylakoid membrane integrity. Associated with photosynthetic electron transport is a vectoral movement of protons from the exterior to the interior of the membrane vesicles. The energy of this proton gradient is ultimately used to synthesize ATP. 9-aminoacridine is a fluorescent compound whose fluorescence is quenched when the concentration of protons increases in the interior of the thylakoid membrane. The assay, then, involves measuring the fluorescence intensity of 9-AA treated thylakoids in the dark and then exposing them to moderate intensity actinic light. The actinic light drives electron and proton transport, resulting, in an intact system, in a decrease in the 9-AA fluorescence. Any treatment that blocks reaction center and electron transport function or damages the integrity of the membrane will decrease the extent of this quenching of 9-AA fluorescence.

When the membranes were dried, stored, and rehydrated, a marked decrease in this quenching was noted. However, as shown in FIG. 7, when they were dried in the presence of sucrose, the decrease was attenuated.

Vitrification, or the glassy state, is a state of a liquid in which there is a very high viscosity. Vitrification can be considered to be a formation of a highly viscous liquid, as a consequence of the inability to crystallize. The soluble sugars are ordinarily good vitrifiers, and as the water content is pulled down or the temperature is depressed, a good glass transition is ordinarily observed.

Many common substances have the property of vitrification; that is, they will form a glassy solid state under certain conditions. Among these substances are several sugars, including sucrose and maltose, and other more complex compounds, such as polyvinyl pyrolidone (PVP). As any solution dries down, the molecules in the solution can either crystallize, or they can vitrify. A solute which has an extensive assymmetry may be a superior vitrifier, because of the hindrances to nucleation of crystals during drying. As noted above, the addition of raffinose inhibits the crystallization of sucrose, and hence improves the protective effects.

Some vitrifying compounds are unsuitable for the protective function, as they themselves initiate harmful reactions. However, any vitrifying substance which does not itself initiate a harmful reaction can serve the protective function. The mechanism of action of such vitrifying substances indicates that they can be used to protect nucleic acids, membranes, organelles, spores, seeds, and small organisms, as well as proteins and lipids, from drying and degradation during storage.

Figure 8:
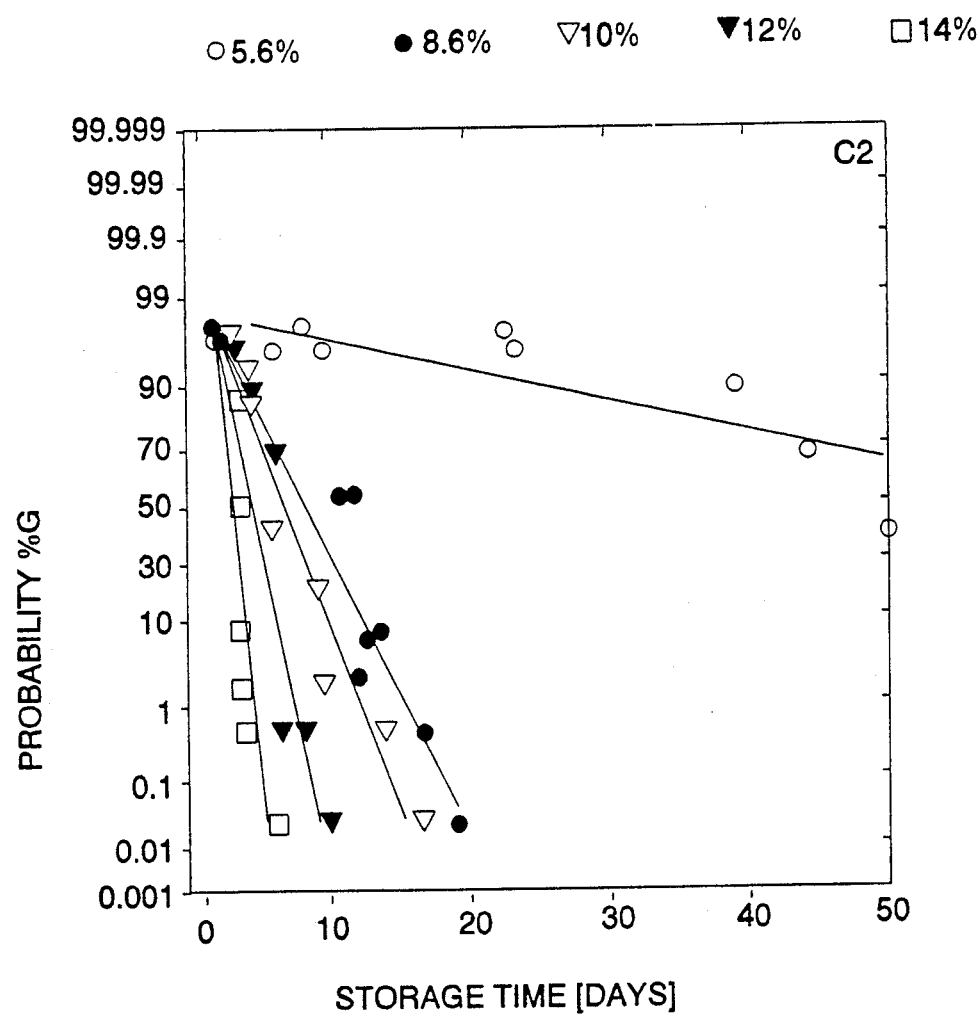
FIG. 8 is a graph depicting the germination rates of corn seeds stored at various moisture levels.

This is further demonstrated by experiments with corn seeds. FIG. 8 shows the results achieved when corn seeds were stored with various degrees of moisture content (determined by International Seed Testing Association methods). Although a "dry" substance will always have some moisture content, the level of moisture is very important for the vitrification of the protective substances; each vitrifying substance achieves the vitrified (amorphous solid) state only at or below a certain moisture content.

The seeds were equilibrated to various moisture contents at 4 degrees Centigrade, stored at 50 degrees C. for a period of time, then tested for germinability. Corn seeds contain several vitrifying substances as natural protectants, and the effectiveness of the protection against destructive reactions is indicated by the percentage of seeds that subsequently germinate. The results show that the protective effect is only achieved when the seeds are stored in a sufficiently dry state (less than 8.6% moisture content) to allow the protective substances to become vitrified.

The teachings of the present invention apply equally to cells, including the cells of the type incorporated in the referenced publications. For example, free living rhizobia cultured from the stem nodules of Sesbania rostrata were mixed with 10% (W/v) sucrose:raffinose and dried over $P_2O_5$ at 4° C. for 3 days. At the end of the incubation period the dried material was resuspended in the original growth media and assayed for respiratory activity with an oxygen electrode. Those cells which had been dried in the presence of the sucrose:raffinose displayed a 5 fold higher respiratory activity over the cells which had been dried in the absence of the sucrose:raffinose.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

What is claimed is:

1. A method of protecting biological materials selected from the group consisting of tissues, cells, organelles, and biologically active compounds from drying and from destructive reactions which take place during storage, comprising the steps of:
   (a) selecting a mixture including cells such as living rhizobia cells;
   (b) combining said mixture with sufficient quantity of one or more vitrifying solutes to protect said mixture during drying and to inhibit said destructive reactions,
   (c) drying said combination, by exposing said combination to a desiccant, at a temperature above that at which said combination will freeze and below that at which said vitrifying solutes achieve the vitrified state, at approximately normal atmospheric pressure, until said combination is substantially dry, and
   (d) storing said combination in a dry state.

2. The method of claim 1, wherein said mixture further comprises one or more destructive substances which would, in the absence of a protective effect, initiate said destructive reactions.

3. The method of claim 2, wherein said destructive substances include a reducing sugar.

4. The method of claim 3, wherein said reducing sugar is glucose.

5. The method of claim 2, wherein said destructive substances include a free-radical generating substance.

6. The method of claim 5, wherein said free-radical generating substance is riboflavin.

7. The method of claim 2, wherein said vitrifying solutes include at least one non-reducing sugar.

8. The method of claim 1, wherein said vitrifying solutes include at least one non-reducing sugar.

9. The method of claim 8, wherein said non-reducing sugars include sucrose.

10. The method of claim 9, wherein said non-reducing sugars includes an oligosaccharide.

11. The method of claim 10, wherein said oligosaccharide is raffinose.

12. The method of claim 11, wherein said sucrose and raffinose are in present in a 3:1 mass ratio.

13. The method of claim 8, wherein said non-reducing sugars include raffinose.

14. A composition produced by a method of preparing materials to be stored in a dry state comprising the steps of:
   a. selecting a mixture including cells such as living rhizobia cells,
   b. combining said mixture with sufficient quantity of one or more vitrifying solutes to protect said mixture during drying and to inhibit said destructive reactions, and
   c. drying said combination, by exposing said combination to a desiccant, at a temperature above that which said combination will freeze and below that at which said vitrifying solutes achieve the vitrified state, at approximately normal atmospheric pressure, until said combination is substantially dry.

15. A composition of protected biological materials in the dry state, comprising a combination of biological materials including cells such as living rhizobia cells, and one or more vitrified solutes, wherein said vitrified solutes are present in sufficient quantity to protect said biological materials from destructive reactions which render said materials less biochemically active over time.

16. The composition of claim 15, further comprising one or more destructive substances which would, in the absence of a protective effect, initiate said destructive reactions.

17. The composition of claim 16, wherein said destructive substances include a reducing sugar.

18. The composition of claim 17, wherein said reducing sugar is glucose.

19. The composition of claim 16, wherein said destructive substances include a free-radical generating substance.

20. The composition of claim 19, wherein said free-radical generating substance is riboflavin.

21. The composition of claim 15, wherein said vitrified substances include at least one non-reducing sugar.

22. The composition of claim 21, wherein said non-reducing sugars include sucrose.

23. The composition of claim 22, wherein said non-reducing sugars includes an oligosaccharide.

24. The composition of claim 23, wherein said oligosaccharide is raffinose.

25. The composition of claim 24, wherein said sucrose and raffinose are in present in a 3:1 mass ratio.

26. The composition of claim 21, wherein said non-reducing sugars include raffinose.

27. A composition comprising the parts of:
   a. one or more vitrifying solutes capable of protecting cells such as living rhizobia cells during drying and from destructive reactions which take place during storage of said cells, and
   b. a desiccant, used to dry said vitrifying solutes and said cells at a temperature above that at which said vitrifying solutes and said cells will freeze and below that at which said vitrifying solutes achieve the vitrified state, at approximately normal atmospheric pressure, until said vitrified solutes and said cells are substantially dry.

* * * * *